United States Patent [19]

Wheeler

[11] 4,436,666

[45] * Mar. 13, 1984

[54] BIOCIDAL ENOL DERIVATIVES OF 2-ARYL-1,3-CYCLOALKANEDIONE COMPOUNDS

[75] Inventor: Thomas N. Wheeler, Charleston, W. Va.

[73] Assignee: Union Carbide Corporation, Danbury, Conn.

[ * ] Notice: The portion of the term of this patent subsequent to Jun. 24, 1997 has been disclaimed.

[21] Appl. No.: 945,005

[22] Filed: Sep. 22, 1978

[51] Int. Cl.$^3$ .................. C07C 154/00; C07C 69/96
[52] U.S. Cl. .................. 260/455 B; 260/463; 260/465 D; 260/465 F; 71/100; 71/105; 71/106; 71/123; 424/301; 424/304; 424/331; 568/327; 568/328; 568/329; 568/330
[58] Field of Search .................. 71/100, 106, 123; 424/301; 260/455 B, 463; 568/327, 328, 329

[56] References Cited

U.S. PATENT DOCUMENTS

| | | | |
|---|---|---|---|
| 3,273,992 | 9/1966 | Treves et al. | 71/123 |
| 3,419,620 | 12/1968 | Becher et al. | 260/455 B |
| 3,742,008 | 6/1973 | Krenzer et al. | 71/100 |
| 3,820,975 | 6/1974 | Poje et al. | 260/455 B |
| 3,830,829 | 8/1974 | Olin | 71/100 |
| 3,852,359 | 12/1974 | Dunbar et al. | 71/103 |
| 4,033,754 | 7/1977 | Sawaki et al. | 71/106 |
| 4,104,043 | 8/1978 | Durden, Jr. et al. | 71/106 |
| 4,209,532 | 6/1980 | Wheeler . | |

FOREIGN PATENT DOCUMENTS 7009285 1/1971 Netherlands .................. 71/122

OTHER PUBLICATIONS

Grens et al., "Nature of Associations, etc.," (1972), CA 78, No. 110026f, (1973).
Correla et al., "Molecular Rearrangements, etc.," (1969), CA 71, No. 38487t, (1969).
Severin et al., "Quinoid Diazo Compds." (1964), CA 62, pp. 6595–6596 (1965).

*Primary Examiner*—Glennon H. Hollrah
*Attorney, Agent, or Firm*—E. A. Forzano; D. L. Carlson; G. L. Coon

[57] ABSTRACT

Enol derivatives of 2-aryl-1,3-cycloalkanedione compounds exhibit outstanding herbicidal and acaricidal activity.

21 Claims, No Drawings

BIOCIDAL ENOL DERIVATIVES OF 2-ARYL-1,3-CYCLOALKANEDIONE COMPOUNDS

This invention relates to biocidal enol derivatives of 2-aryl-1,3-cycloalkanedione compounds as well as methods of preparing them. This invention is also directed to herbicidal and acarcidal compositions as well as methods of controlling these plant pests which utilize the compounds of the instant invention as the pesticidally effective component.

More particularly, the compounds employed as the pesticidally active components in the above compositions are enol derivatives of 2-phenyl-1,3-cyclohexanedione compounds or 2-phenyl-1,3-cyclopentadione compounds. These derivatives are thiocarbonate, carbonate, bis-ester or ether derivatives of the enol compounds.

The instant invention relates to compounds characterized by the following formula:

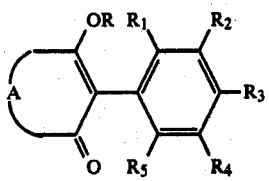

wherein:

wherein:

R' may not include more than thirty aliphatic carbons and is selected from: an unsubstituted or substituted alkyl, alkenyl, alkynyl, bicycloalkyl, bicycloalkenyl, cycloalkyl, cycloalkenyl, phenyl, phenylalkyl, naphthyl, or naphthylalkyl group wherein the permissible substituents are one or more alkyl, cyano, nitro, alkoxy, aryloxy, halogen, haloalkyl, alkylthio, arylthio, alkylsulfinyl, arylsulfinyl, alkylsulfonyl, arylsulfonyl alkoxyalkyl, aryloxyalkyl, alkylthioalkyl, arylthioalkyl, alkylsulfinylalkyl, arylsulfinylalkyl, alkylsulfonylalkyl arylsulfonylalkyl, or dialkylamino groups in any combination;

R" is a divalent moiety which may not include more than thirty aliphatic carbon atoms and is selected from an unsubstituted or substituted alkylene, alkenylene, alkynylene, bicycloalkylene, bicycloalkenylene, cycloalkylene, cycloalkenylene, phenylene, phenylalkylene, naphthylene, or naphthylalkylene group wherein the permissible substituents are one or more alkyl, cyano, nitro, alkoxy, aryloxy, halogen, haloalkyl, alkylthio, arylthio, alkylsulfinyl, arylsulfinyl, alkylsulfonyl, arylsulfonyl, alkoxyalkyl, aryloxyalkyl, alkylthioalkyl, arylthioalkyl, alkylsulfinylalkyl, arylsulfinylalkyl, alkylsulfonylalkyl, arylsulfonylalkyl or dialkylamino groups, in any combination;

$R_1$ may not individually include more than ten aliphatic carbon atoms and is an alkyl, haloalkyl, halogen or polyhaloalkyl group;

$R_2$, $R_3$, $R_4$ and $R_5$ may not individually include more then ten aliphatic carbon atoms and are individually hydrogen, nitro, polyhaloalkyl, halogen, cyano, alkyl, alkoxy, alkylthio, alkysulfinyl, alkylsulfonyl, alkanoyl amido, amino or haloalkyl groups;

A is an alkylene or alkenylene chain containing two or three carbon atoms which may be substituted by one or more substituents which may be the same or different selected from:

(a) substituents which may not include more than ten aliphatic carbon atoms selected from: an alkyl, alkenyl, cycloalkyl or cycloalkenyl groups, which groups may be further substituted with one or more cyano, halogen, nitro, alkoxy, aryloxy, alkythio, arylthio, alkylsulfinyl, arylsulfinyl, alkylsulfonyl, arylsulfonyl, acylamido, or dialkylamino substituents in any combination; and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents in any combination;

(b) a divalent alkylene or alkenylene group having from 2 to 20 carbon atoms completing a 3,4,5,6 or 7 membered carbon ring with the proviso that when A is a hydrocarbon chain containing two carbon atoms, said hydrocarbon chain may not form together with said divalent alkylene group a six membered fused polycyclic ring structure wherein said six membered ring has more than two double bonds.

Further, the instant invention relates to compounds wherein the carbonate, thiocarbonate, bisester moiety itself comprises a 2-phenyl-1,3-cycloalkanedione component, which compounds are defined by the following formula:

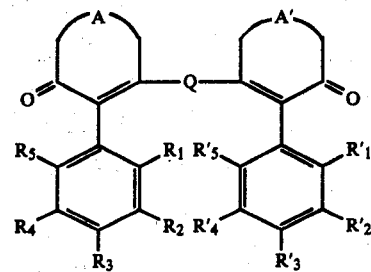

wherein:
Q is

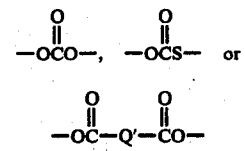

Q' is a divalent moiety which may not include more than thirty aliphatic carbon atoms and is selected from an unsubstituted or substituted alkylene, alkenylene, alkynylene, bicycloalkylene, bicycloalkenylene, cycloalkylene, cycloalkenylene, phenylene, phenylalkylene, naphthylene, or naphthylalkylene group wherein the permissible substitutents are one or more alkyl, cyano, nitro, alkoxy, aryloxy halogen, haloalkyl, alkylthio, arylthio, alkylsulfinyl, arylsulfinyl, alkylsulfonyl, arylsulfonyl, alkoxyalkyl, aryloxyalkyl, alkylthioalkyl, arylthioalkyl, alkylsulfinylalkyl, arylsulfinylalkyl, alkylsulfonylalkyl arylsulfonylalkyl or dialkylamino groups; in any combination;

$R_1$ and $R_1'$ may not individually include more than ten aliphatic carbon atoms and are individually alkyl haloalkyl, halogen or polyhaloalkyl groups;

$R_2$ to $R_5$ inclusive and $R_2'$ to $R_5'$ inclusive may not individually include more than ten aliphatic carbon atoms and are individually hydrogen, nitro, polyhaloalkyl, halogen, cyano, alkyl, alkoxy, alkylthio, alkylsulfinyl, alkylsulfonyl, alkanoyl, amido, amino or haloalkyl groups;

A and A' are individually an alkylene or alkenylene chain containing two or three carbon atoms which may be substituted by one or more substituents which may be the same or different selected from:

(a) substituents which may not include more than ten aliphatic carbon atoms selected from: an alkyl, alkenyl, cycloalkyl or cycloalkenyl groups, which groups may be further substituted with one or more cyano, halogen, nitro, alkoxy, aryloxy, alkythio, arylthio, alkylsulfinyl, arylsulfinyl, alkylsulfonyl, arylsulfonyl; acylamido, or dialkylamino substituents in any combination; and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents in any combination;

(b) a divalent alkylene or alkenylene group having from 2 to 20 carbon atoms completing a 3, 4, 5, 6 or 7 membered carbon ring with the proviso that when A or A' is a hydrocarbon chain containing two carbon atoms, said hydrocarbon chain may not form together with said divalent alkenylene group, a six membered fused polycyclic ring structure, wherein said six membered ring has more than two double bonds.

As used within this specification the prefix "aryl" designates any organic radical derived from an aromatic hydrocarbon by the removal of one hydrogen atom. Preferably, aryl designates a phenyl or naphthyl moiety.

PREFERRED EMBODIMENT OF THE INVENTION

All compounds within the purview of the above generic formula exhibit acaridical and herbicidal activity to a greater or lesser extent. Some of these compounds exhibit very powerful acaricidal or herbicidal activity in extremely small dosages while others require larger dosages to be pesticidally effective. In general, the compounds of this invention that exhibit the highest order of herbicidal activity also exhibit the highest order of acaricidal activity. The compounds of the instant invention are particularly effective against mites, both in the egg stage and the adult stage. Acaricidal and herbicidal activity is greatest in those compounds having an alkyl or halogen group at one ortho position of the 2-phenyl moiety and a hydrogen, alkyl, alkoxy, cyano, trihalomethyl or halogen substituent at either the para position or the other ortho position of the phenyl moiety. Especially active compounds are those in which the ortho substituents are relatively small groups, such as methoxy, ethoxy, methyl, ethyl, hydrogen or halogen.

It has also been found that some of the pesticidal compositions of this invention exhibit excellent fumigant properties. Fumigant activity is defined as the ability of a pesticide to exert its pesticidal activity on an untreated surface or plant from a treated surface or plant in close proximity to the untreated area. It is believed that this property is caused, at least in part, by the low vapor pressure of the compounds allowing them to volatilize from a treated surface thereby exerting their pesticidal effects on nearby untreated areas. In addition, these compounds are relatively non-toxic to mammals when used in amounts sufficient to kill acarids or undesirable plant growth.

The preferred cyclopentanedione compounds of the instant invention due to their higher level of acaricidal and herbicidal activity are those of the following formula:

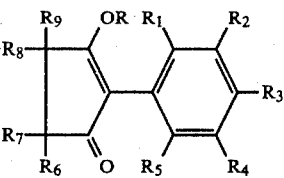

wherein:

R is as defined above;

R' may not include more than 18 aliphatic carbon atoms and is selected from an alkyl, alkenyl, alkynyl, phenyl, phenylalkyl, naphthyl or napthylalkyl group, all of which may be unsubstituted or substituted with one or more chloro, alkoxy, alkylthio or alkyl groups in any combination; and R" is a divalent moiety which may not include more than 18 aliphatic carbon atoms and is selected from an alkylene, alkenylene, alkynylene, phenylene, phenylalkylene, naphthylene or naphthylalkylene group all of which may be unsubstituted or substituted with one or more chloro, alkoxy, alkylthio or alkyl groups in any combination.

$R_1$ is an alkyl or halogen;

$R_2$, $R_3$, $R_4$ and $R_5$ are individually hydrogen, alkyl, cyano, alkoxy, halogen or trihalomethyl groups;

$R_6$ and $R_8$ are hydrogen; and $R_7$ and $R_9$ are individually hydrogen or alkyl groups, particularly methyl.

The preferred cyclohexanedione compounds of the instant invention are those in which R, R', R", $R_1$, $R_2$, $R_3$, $R_4$ and $R_5$ are as defined for the preferred cyclopentanedione compounds above; and A is a saturated hydrocarbon group containing three carbon atoms which group may be substituted by one or more $C_1$–$C_6$ alkyl groups, particularly methyl.

The preferred compounds of the formula:

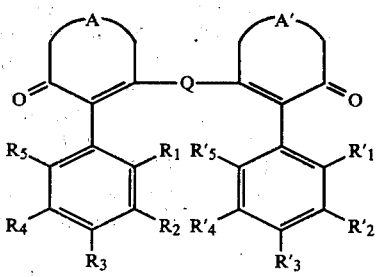

are those in which:

Q is

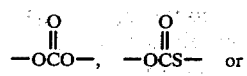

-continued

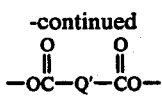

Q' is an alkylene or alkenylene group which may not include more than 18 aliphatic carbon atoms; and $R_1$, $R_2$, $R_3$, $R_4$, $R_5$ and A are as defined above for the preferred cyclohexanedione or cyclopentanedione compounds of the instant invention, defined above.

The most active and particularly preferred compounds of the instant invention are those of the following formulae:

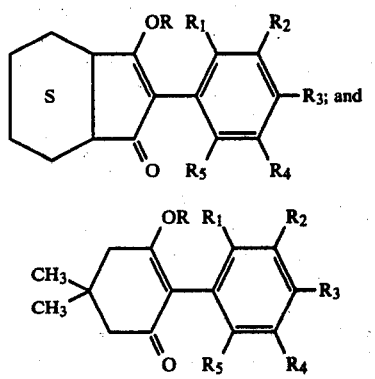

especially those in which the substituents are defined as follows:

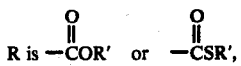

especially when

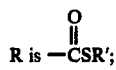

R' is a $C_1$–$C_{18}$ alkyl group; a phenyl group; or a $C_7$–$C_{12}$ phenylalkyl group unsubstituted or substituted with one or two chloro groups; and R" is a $C_1$–$C_{18}$ alkylene group; a phenylene group; or a $C_7$–$C_{12}$ phenylalkylene group;

$R_1$ is alkyl, particularly methyl or halogen, particularly chlorine;

$R_2$, $R_4$ and $R_5$ are hydrogen; and $R_3$ is alkyl, particularly methyl, or halogen, particularly chlorine.

It should be noted that the cyclohexanedione compounds above are especially preferred.

The individually preferred compounds of this invention are:

[2-(2',4'-dimethylphenyl)-3-oxo-5,5-dimethyl-1-cyclohexenyl][isopropyl]thiocarbonate;

[2-(2'-methylphenyl)-3-oxo-5,5-dimethyl-1-cyclohexenyl][phenyl]thiocarbonate;

[2-ethylhexyl][2-(2'4'-dimethylphenyl)-3-oxo-5,5 dimethyl-1-cyclohexenyl]carbonate

[2-ethylhexyl][2-(2'-methylphenyl)-3-oxo-4,5,6,7,8,9-hexahydro-1-indenyl]carbonate; and 3-(5-carbomethoxypentanoyloxy)-2-(2'-4'-dimethylphenyl)-5,5-dimethyl-2-cyclohexenone.

The compounds of this invention are prepared by a variety of methods.

The bisester, carbonate and thiocarbonate enol derivatives of the 2-phenyl-1,3-cycloalkanedione compounds can be prepared according to the general reaction scheme set forth below wherein R', R", $R_1$–$R_5$ and A are as described previously and X is a halogen, preferably chlorine, and R is limited to the following:

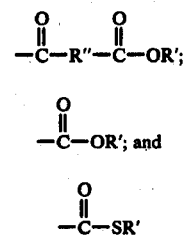

Reaction Scheme I

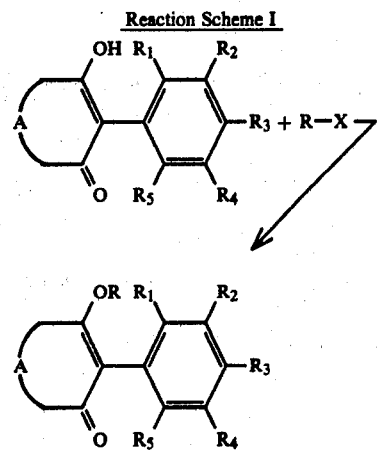

In the above reaction scheme, the 2-phenyl-1,3-cycloalkanedione compound is reacted with:

(a) the appropriate ester acid halide compound, i.e., when R is

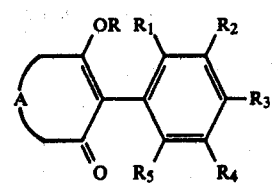

to synthesize the enol bisester derivative compounds;

(b) the appropriate haloformate compound, i.e., when R is

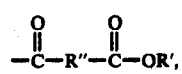

to prepare the enol carbonate derivative compounds; and (c) the appropriate thiohaloformate compound, i.e., when R is

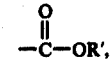

to synthesize the enol thiocarbonate derivative compounds of the instant invention.

It is understood that the bisester, carbonate and thiocarbonate enol derivatives of the following formula:

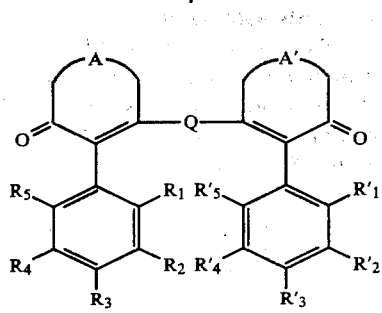

can be made by reaction scheme I.

The 2-phenyl-1,3-cycloalkanedione compound is reacted with:

(a) the appropriate ester acid halide of the formula:

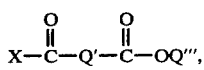

to synthesize the enol biester derivative compounds;

(b) the appropriate haloformate compound of the formula:

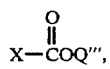

to prepare the enol carbonate derivative compounds; and (c) the appropriate thiohaloformate compound of the formula:

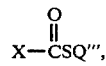

to synthesize the enol thiocarbonate derivative compounds of the instant invention. In the above description Q''' is a monovalent cycloalkanedione moiety of the following structure:

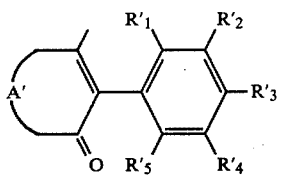

In each of these reactions, one equivalent of the 2-phenyl-1,3-cycloalkanedione compound is reacted with the appropriate reactant in the presence of at least one equivalent of an acid acceptor, preferably in an inert solvent.

The acid acceptor utilized in the above reaction scheme can be either an organic or inorganic base. Illustrative of organic bases that are useful as acid acceptors are tertiary amines, such as triethylamine, pyridine, trimethylamine or 1,4-diazobicyclo [2.2.2] octane; or alkali metal alkoxides, as, for example, sodium ethoxide; potassium hydroxide and sodium hydroxide are illustrative of inorganic bases that are useful as acid acceptors. Preferred acid acceptors are N,N-dimethylaniline, triethylamine, pyridine or trimethylamine.

In general, any organic solvent that is inert to the reactants or reaction conditions may be employed in the reaction scheme shown above. Illustrative of organic solvents which are generally suitable for use in the conduct of these reactions are saturated, unsaturated and aromatic hydrocarbons, e.g. hexane, cyclohexane, octane, cyclohexane, dodecane, naphtha, decalin, kerosene, cycloheptane, benzene, toluene, xylene, naphthalene or the like; ethers such as dioxane, tetrahydrofuran, diethyl ether, tetrahydropyran, 1,2-dimethoxybenzene, 1,2-diethylbenzene, the dialkyl ethers of ethylene glycol, of propylene glycol or chlorinated aliphatic hydrocarbons as, for example, chloroform, dichloromethane, 1,1-dichloroethane, carbon tetrachloride, or the like.

The reactions illustrated by the general scheme given above may also be conducted in a solvent which functions as an acid acceptor. Illustrative of such multifunctional solvents are N,N-dimethylaniline, pyridine, α-picoline, any lutidine, collodine or any like aromatic or heterocyclic tertiary amine compound.

The reactions illustrated by the general scheme given above are neither temperature nor pressure sensitive and can be conducted over a broad temperature and pressure range to yield the desired product. Preferably, these reactions are conducted at a temperature of from $-40°$ C. to about $120°$ C. and at atmospheric or autogeneous pressure.

The enol ether compounds of the instant invention are prepared according to the following reaction scheme wherein A, R, $R_1$ and $R_n$ represents $R_2$, $R_3$, $R_4$ and $R_5$ as defined above.

Reaction Scheme II

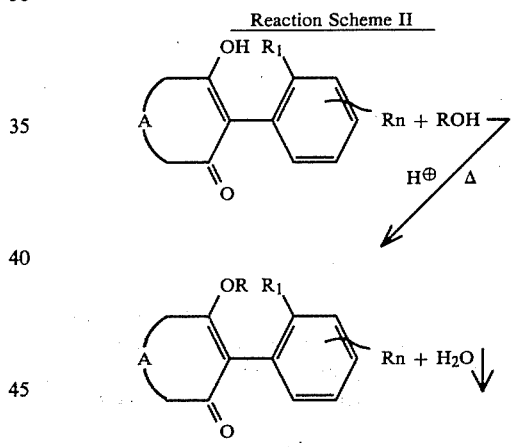

In this reaction, the 2-phenyl-1,3-cycloalkanedione compound is reacted with an appropriate alcohol in the presence of an acid catalyst under such conditions that the water of dehydration is removed. The water of dehydration is removed by conventional methods such as the azeotropic removal of the water or by refluxing the reaction mixture through a molecular sieve that will remove the water.

Illustrative of the acid catalysts that can be used in this reaction are any mineral acids such as hydrochloric acid or sulfuric acid and organic acids such as methanesulfonic acid or para-toluene sulfonic acid.

In general, any organic solvent that is inert to the reactants and the reaction conditions may be employed in the reaction scheme shown above. Illustrations of these solvents are presented above for reaction scheme I.

The reaction illustrated by reaction scheme II is neither temperature nor pressure sensitive and can be conducted over a broad temperature and pressure range to yield the desired product. Preferably, these reactions are conducted at a temperature from about 25° to 175° C. and at atmospheric or autogeneous pressure.

An alternative method of preparing the enol ethers of the instant invention comprises reacting the alkali metal salts of the 2-phenyl-cycloalkanedione compounds with the appropriate alkyl halide in an inert solvent. Examples of alkyl halides include any primary or secondary alkyl halide such as methyl chloride, N-propyl bromide or haloalkyl ethers, for example, chloromethyl methyl ether.

The inert solvent and the reaction conditions are as defined above for reaction scheme I.

Alternative methods of preparation are presented below for the synthesis of the compounds of the instant invention. Unless otherwise noted, acid acceptors, solvents and reaction conditions are as defined for reaction scheme I.

Both the enol carbonate and thiocarbonate compounds of the instant invention can be prepared in two steps according to reaction scheme III wherein A, R₁ and Rn are as defined above.

Reaction Scheme III

Step A

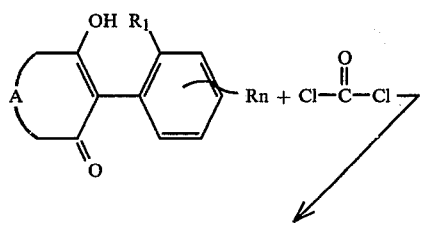

Step B

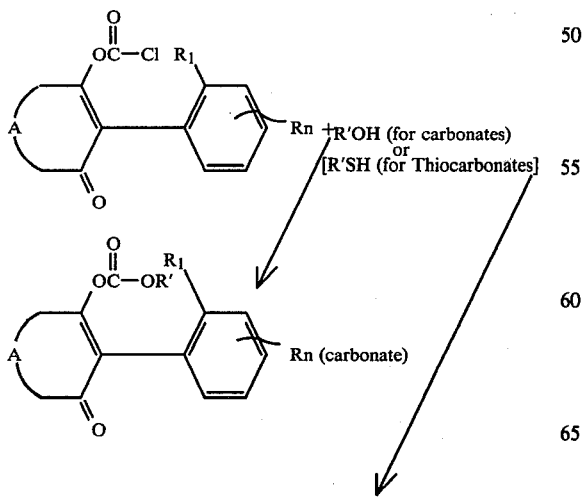

-continued
Reaction Scheme III

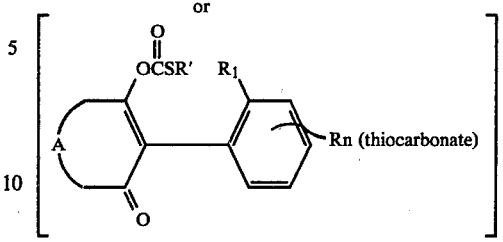

In Step A, the enol chloroformate derivative of the 2-phenyl-1,3-cycloalkanedione compound is prepared by reacting the 2-phenyl-1,3-cycloalkanedione compound with excess phosgene in the presence of a weak acid acceptor in an inert solvent. Examples of weak acid acceptors include N,N-dialkylaniline compounds such as N,N-dimethylaniline and N,N-diethylaniline, and so on.

In Step B, one equivalent of the enol chloroformate derivative compound is reacted with either the appropriate alcohol (to obtain the carbonate compound) or the appropriate mercaptan compound (to obtain the thiocarbonate compound) in the presence of an acid acceptor, preferably in an inert solvent.

Alternately, the above reaction scheme can be reversed by first preparing the chloroformate or thiochloroformate compound by reacting phosgene with either the appropriate mercaptan compound or the appropriate alcohol (the reactants in step B, above) in the presence of an acid acceptor. The chloroformate or thiochloroformate prepared in the above step is then reacted with the appropriate 2-phenyl-1,3-cycloalkanedione in the presence of an acid acceptor to obtain the desired compound.

An alternative method of preparing symmetrical bis-ester compounds is illustrated by reaction scheme IV. In this scheme, A, R₁, Q" and Rn are as defined above and X is a halogen, preferably chlorine.

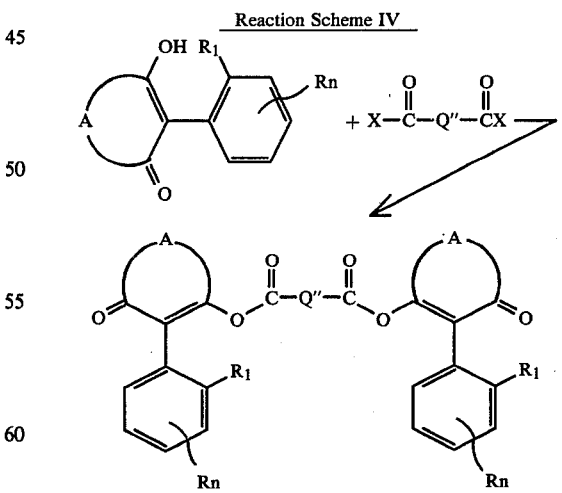

In this reaction, 2 equivalents of the 2-phenyl-1,3-cycloalkanedione are reacted with one equivalent of a dicarboxylic acid halide, preferably the dichloro derivative, in the presence of at least two equivalents of an acid acceptor in an inert solvent.

Symmetrical enol biscarbonates of the instant invention can be prepared by a similar method as reaction scheme IV. In that reaction two equivalents of the 2-phenyl-1,3-cycloalkanedione compound is reacted with phosgene in the presence of at least two equivalents of an acid acceptor in an inert solvent to obtain the desired compound.

The reactants in the above reaction scheme can be prepared or obtained as set forth below.

The haloformate, thiohaloformate and ester acid halide compounds utilized as reactants in reaction scheme I are known classes of compounds that can be obtained from commercial sources or prepared in accordance with conventional methods known to those skilled in the art.

The alkali metal salts of 2-phenyl-1,3-cycloalkanedione compounds used as reactants in the preparation of the enol ether compounds of the instant invention can be prepared by conventional methods. For example, the alkali metal and ammonium salts can be prepared by treating the corresponding 2-phenyl-1,3-cycloalkanedione compound with an alkali metal alkoxide, or ammonia or an amine respectively.

The 2-phenyl-1,3-cycloalkanediones utilized as reactants in the above synthesis schemes can be conveniently prepared by a number of synthesis methods.

For example, the 2-aryl-1,3-cyclopentanediones may be prepared by the base-promoted cyclization of the appropriate δ-aryl levulinic acid ester. This is illustrated by reacting ethyl-5-(2',4'-dichlorophenyl)-4-ketopentanoate with sodium ethoxide in the presence of a toluene solvent to form 2-(2',4'-dichlorophenyl)-1,3-cyclopentanedione. The δ-aryl levulinic acid esters used as reactants in the above synthesis can be prepared using conventional esterification techniques of the appropriate δ-aryl levulinic acids.

The 8-arylbicyclo[4.3.0]nonane-7,9-diones are prepared by the base promoted isomerization of the appropriate γ-benzylidene lactone. This is illustrated by reacting 4, 5, 6, 7, 8, 9-hexahydro-3-(2'-methylbenzylidene)phthalide with sodium ethoxide in the presence of a toluene solvent to form 8-(2'-methylphenyl)-bicyclo[4.3.0]nonane-7,9-dione. The γ-benzylidene lactone can be formed by the acid catalyzed lactonization of the corresponding δ-aryl levulinic acid, a synthesis method known to those skilled in the art.

Preferably, those 2-aryl-1,3-cyclopentanedione compounds, wherein (1) there is a fused ring on the cyclopentane moiety and (2) the 2-phenyl substituent is itself substituted with halogens, may be formed by pinacol rearrangement as outlined in the Journal of The American Chemical Society, (99:3) Feb. 2, 1977, pages 961–962. These synthetic procedures are described in more detail in my copending U.S. patent application Ser. No. 197,600, filed Oct. 16, 1980, now U.S. Pat. No. 4,338,122, Entitled "Biocidal 2-Aryl-1,3-Cyclopentanedione Compounds and Alkali Metal and Ammonium Salts Thereof".

The 2-aryl-1,3-cyclohexanedione compounds utilized as reactants in the above reaction schemes also can be conveniently prepared in accordance with a number of synthetic procedures. For example, 2-aryl-1,3-cyclohexanedione compounds in which the ortho position on the 2-phenyl moiety other than $R_1$ is hydrogen can be prepared by heating the corresponding 6-aryl-5-ketopolyalkyl hexanoic acid compound with sulfuric acid or alternatively by treating the corresponding 6-aryl-5-ketopolyalkylhexanoic acid ester with base. The 2-aryl-cyclohexane-1,3-dione compounds in which at least one ortho substituent is alkyl and the other ortho substituent is other than hydrogen, can be conveniently prepared by the benzophenone sensitized photolysis of the corresponding 2-diazocyclohexane-1,3-dione compound in an appropriately substituted aromatic solvent.

The remaining 2-aryl-1,3-cyclohexanedione precursors can be conveniently prepared by reacting the corresponding 1,3-cyclohexanedione compound with an appropriately substituted halobenzene compound. These synthetic procedures are described in more detail in my copending U.S. patent application Ser. No. 781,985, entitled "Biocidal 2-Aryl-1,3-Cyclohexanedione Compounds and Alkali/metals and Ammonium Salts Thereof," filed Mar. 28, 1977 now U.S Pat. No. 4,209,532.

The following specific examples are presented to more particularly illustrate the processes of this invention and its use in preparing the compounds of this invention:

EXAMPLE I

Preparation of 3-chlorocarbonyloxy-2-(2',4'-dimethylphenyl)-5,5-dimethyl-2-cyclohexenone A clean, dry 500 ml single-neck round bottom flask was equipped with a magnetic stirrer and 250 ml addition funnel. The flask was charged with 204 ml of 0.50 N phosgene/toluene solution (0.102 mol) and cooled to 0° C. with a surrounding ice bath. A solution of 10.00 g (0.0410 mol) of 2-(2',4'-dimethylphenyl)-5,5-dimethyl-1,3-cyclohexanedione and 5.47 g (0.0451 mol) of N,N-dimethylaniline in 100 ml of methyl chloride was prepared and added dropwise to the solution. The mixture was stirred for 2 hrs. at 0° C., then placed in a refrigerator overnight. The excess phosgene and solvents were removed under vacuum at a temperature which never exceeded 42° C. A blue colored residue remained. Anhydrous ether was added to this residue and the solution filtered. The ether was removed under vacuum, and the residue was taken up in hexane and cooled. A white, crystalline solid former, which was collected by suction filtration was washed several times with hexane. After drying in a vacuum desiccator, 8.87 g (71% yield) of white crystals, m.p. 65°–67° were obtained. This material was very hydroscopic and decomposed at room temperature after several hours.

The compound prepared by the above synthesis has the following structure:

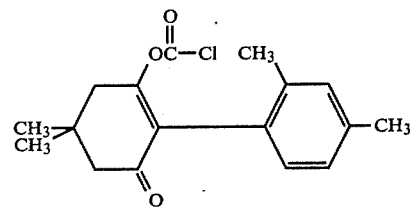

EXAMPLE II

Preparation of [3',4'-Dichlorobenzyl](2,2',4'-dimethylphenyl)-3-oxo-5,5-dimethyl-1[cyclohexenyl]carbonate The enol chloroformate was prepared as described above Example I by adding 5.00 g (0.0205 mol) of 2-(2',4'-dimethylphenyl)-5,5-dimethyl-1,3-cyclohexanedione and 3.73 g (0.0308 mol) of N,N-dimethylaniline in 50 ml of methylene chloride to 102 ml (0.0512 mol) of 0.5 N phosgene/toluene solution at 0° C. The mixture was stirred for 1 hr. at 0° C., 1 hr. at 25° C., the solvent removed below 40° C., and the blue residue was taken up in 25 ml of methylene chloride. This solution was cooled in an ice bath, and a mixture of 2.72 g (0.0154 mol) of 3,4-dichlorobenzyl alcohol and 2.49 g (0.0246 mol) of triethylamine was added dropwise. The reaction mixture was stirred overnight at room temperature and then refluxed for 30 minutes. The solvent was removed, the residue triturated with ether, the amine salt filter off, and the ether washed three times with 50 ml of 0.25 N NaOH, once with ice cold 1 N HCl, and twice with brine solution. The ether solution was dried (MgSO4) and removed to give 7.55 g of crude product. Recrystallization from hexanemethylene chloride gave 3.45 g (38% yield) of white crystals, m.p. 126°-28° C. The compound prepared by the above method has the following structure:

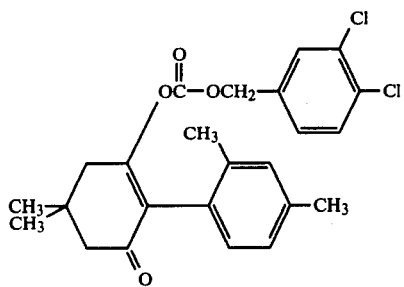

EXAMPLE III

Preparation of
[2-(2',4'-Dimethylphenyl)-3-oxo-5,5-dimethyl-1-cyclohexenyl][isopropyl]thiocarbonate The enol chloroformate was prepared as described in Example I by adding 5.00 g (0.0205 mol) of 2-(2',4'-dimethylphenyl)-5,5-dimethyl-1,3-cyclohexanedione and 3.73 g (0.0308 mol) N,N-dimethylaniline dissolved in 50 ml of methylene chloride to 102 ml (0.0512 mol) of 0.5 N phosgen/toluene solution at 0°. The mixture was stirred for 1 hr. at 0° C., 1 hr. at 25° C., and the solvent and excess phosgene removed below 40° C. on the rotary evaporator. The residue (blue-green in color) was taken up in 25 ml of chloroform (ethanol-free) and 2.34 g (0.0308 mol) of 2-propanethiol in 5 ml of chloroform added to this solution at 0° C. The reaction mixture was stirred for 30 minutes at room temperature and then refluxed for 2 hrs. The solvent was removed, the residue triturated with ether, the amine salt filtered off, and the ether washed three times with 50 ml of 0.25 N NaOH, once with ice cold 1 N HCl, and twice with brine. The ether solution was dried (MgSO4) and removed to leave 7.28 g of a yellow oil. This material was chromatographed by low pressure liquid chromatography (LPLC) using a hexane-ethyl acetate gradient. The solid recovered was recrystallized from hexane to give 2.76 g (39% yield) of a white crystalline solid, m.p. 65°-67° C. The compound prepared by the above synthesis has the following structure:

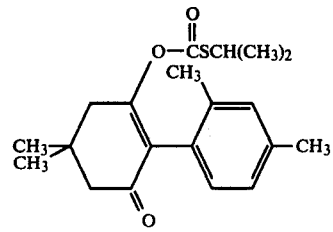

EXAMPLE IV

Preparation of
Bis[2-(2',4'-Dimethylphenyl)-3-oxo-5,5-dimethyl-1-cyclohexenyl]carbonate A solution of 10.00 g (0.0408 mol) 2-(2',4'-dimethylphenyl)-5,5-dimethyl-1,3-cyclohexanedione, 12.38 g (0.122 mol) triethylamine, and 50 ml of toluene was cooled to 0° C. A solution of 82 ml of 0.25 M phosgene/toluene was added dropwise. When the addition was complete, the reaction mixture was stirred at room temperature for 1 hour, then refluxed for 1 hour. The mixture was then cooled to room temperature, the precipitate of triethylamine and HCl was filtered off, and the solvent removed. The residue was taken up in 300 ml of ether, washed with 0.25 N NaOH and 1 N HCl followed by a brine wash. The solution was dried (MgSO4) and the ether removed to leave a very viscous tan oil (8.9 g). This material was chromatographed by LPLC using a hexane-ethyl acetate gradient and the chromatographed material recrystallized from isopropyl ether-hexane to give 4.88 g (46% yield) of white, crystalline solid, m.p. 120°-22° C. The compound prepared by the above synthesis has the following structure:

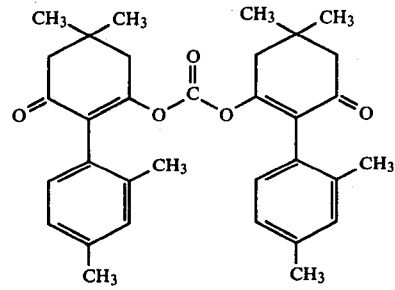

EXAMPLE V

Preparation of
3-Methoxy-2(2',4'-dimethylphenyl)-2-cyclohexenone

A solution of 10.00 g (0.0409 mol) of 2-(2',4'-dimethylphenyl)-5,5-dimethyl-1,3-cyclohexanedione, 21.42 g (0.155 mol) of anhydrous potassium carbonate, 17.59 g (0.124 mol) iodomethane, and 500 ml of anhydrous acetone was refluxed overnight. The reaction mixture was then cooled to room temperature, filtered, and the acetone removed. The residual solid was taken up in 250 ml of CH2Cl2, washed with water, 0.25 N NaOH, 1 N HCl, and water again. The solution was dried (MgSO4) and the solvent removed. The resulting solid was recrystallized from isopropyl ether to give 7.60 g (72% yield) of a white crystalline solid, m.p. 122°-23° C. The compound prepared by the above synthesis has the following structure:

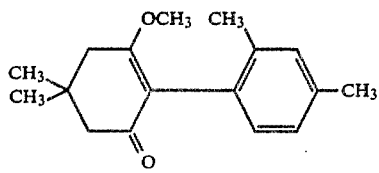

EXAMPLE VI

Preparation of [2-Ethyl hexyl][2-(2'chlorophenyl)-3-Oxo-1-Cyclopentenyl]Carbonate A clean, dry 100 ml single-neck R.B. flask was equipped with a reflux condenser, magnetic stirrer, and nitrogen inlet. The flask was charged with 1.94 g. (9.27 mmol) of 2-(2'-chlorophenyl)-1,3-cyclopentanedione, 1.88 g (18.54 mmol) of triethylamine, 1.43 g (7.42 mmol) of 2-ethylhexylchloroformate, and 25 ml of methylene chloride. The reaction mixture was refluxed for one hour then cooled to room temperature and solvent removed on the rotary evaporator. The residue was triturated with 200 ml of ether, and the ether filtered. The ether was washed with cold 1 N HCl (2×50 ml), water (2×75 ml), dried (MgSO$_4$), and the solvent removed leaving a slightly yellow viscous oil.

Calcd. for $C_{20}H_{25}ClO_4$: C, 65.83; H, 6.91. Found: C, 66.08; H, 6.81.

The compound prepared by the above synthesis has the following structure:

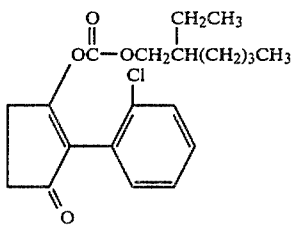

EXAMPLE VII

Preparation of Bis[2-(2',4'-Dimethylphenyl)-3-oxo-5,5-dimethyl-1-cyclohexenyl]sebacate A clean, dry 250 ml single-neck R.B. flask was equipped with a reflux condenser, N$_2$ inlet, and magnetic stirrer. The flask was charged with 5.00 g (0.0205 mol) of 2-(2',4'-dimethylphenyl)-5,5-dimethyl-1,3-cyclohexanedione, 50 ml of methylene chloride, and 3.11 g (0.0308 mol) of triethylamine. To the reaction mixture was added all at once 1.83 g (0.0077 mol) of sebacoyl chloride. The mixture was refluxed for one hour, the solvent removed on the rotary evaporator, and the residue triturated with 250 ml of ether. The ether was filtered, washed with water, with 0.25 N NaOH (3×100 ml), with 1 N HCl (2×75 ml), and with brine. The ether was dried (MgSO$_4$), and the ether removed to give 4.69 g of a slightly yellow, viscous oil.

The reaction was repeated to give 3.63 g of residue product. The two residues were combined to give 8.32 g of crude material which was purified by low pressure liquid chromatography through silica gel using a hexane-ethyl acetate gradient. A total of 6.73 g (67% yield) of the desired product was obtained as a clear, colorless oil.

Calcd. for $C_{42}H_{54}O_6$: C, 77.03; H, 8.31. Found: C, 77.56; H, 8.25.

The compound prepared by the above synthesis has the following structure:

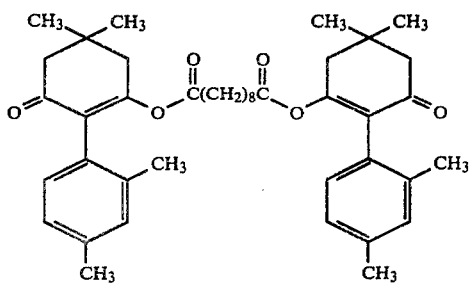

EXAMPLE VIII

Preparation of 3-(5-Carbomethoxy pentanoyloxy)-5,5-dimethyl-2-(2',4'-Dimethylphenyl)-2-Cyclohexenone A clean, dry 250 ml R.B. flask was equipped with a magnetic stirrer, reflux condenser, and N$_2$ inlet. The flask was charged with 10.00 g (0.0409 mol) of 2-(2',4'-dimethylphenyl)-5,5-dimethyl-1,3-cyclohexanedione, 75 ml of methylene chloride, and 8.28 g (0.0818 mol) of triethylamine. To the reaction mixture was added all at once 5.48 g (0.0307 mol) of adipoyl chloride monomethyl ester. The reaction mixture was refluxed for one hour, cooled and the solvent removed on the rotary evaporator. The residue was triturated with 300 ml of ether. The ether was filtered, washed with water, with 0.25 N NaOH (3×100 ml), with cold 1 N HCl (2×75 ml), and with brine. The ether was dried (MgSO$_4$) and removed to give 9.00 g (76% yield) of the desired product as a clear, colorless oil.

Calcd. for $C_{23}H_{30}O_5$: C, 71.48; H, 7.82. Found: C, 70.79; H, 7.99.

The compound prepared by the above synthesis has the following structure:

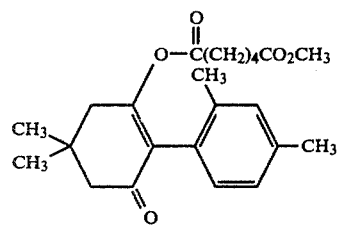

EXAMPLE IX

Preparation of 3-Methoxy methoxy-2-(2',4'-Dimethylphenyl)-4,5,6,7,8,9-hexahydro-2-indenone Chloromethylmethyl ether (3.27 g, 40.60 mmol) was dissolved in toluene and 4.11 g (40.60 mmol) of triethylamine was added with stirring. The triethylammonium hydrochloride salt was filtered off and 23.90 g (8.12 mmol) of the potassium salt of 2-(2',4'-dimethylphenyl)-4,5,6,7,8,9-hexahydro-1,3-indandione was added at room temperature to the filtrate. The reaction mixture was stirred at room temperature for 18 hours.

The reaction mixture was filtered, and the filtrate washed 7× with 0.5 N NaOH, 2× with water, dried (MgSO₄), and the solvent removed to yield an orange oil. This material was purified by low pressure liquid chromatography on silica gel using 90:10 hexane-ethyl acetate to give 9.70 g (40% yield) of a viscous, yellow oil.

Calcd. for $C_{19}H_{24}O_3$: C, 75.47; H, 8.05. Found: C, 75.67; H, 8.00.

The compound prepared by the above synthesis has the following structure:

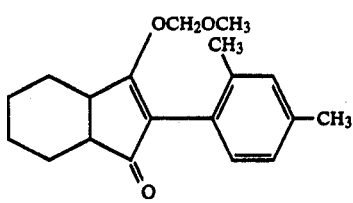

Additional compounds were prepared in a manner sililar to those illustrated in the above examples are listed in Table I with a melting point or an elemental analysis.

The following acaricidal and herbicidal compounds are illustrative of the compounds of the instant invention:

(1) bis[2-(2'-methylphenyl)-3-oxo-5,5-dimethyl-1-cyclohexenyl]succinate
(2) bis[2-(2'-chlorophenyl)-3-oxo-1-cyclopentenyl]glutarate
(3) bis[2-(2',4'-dimethylphenyl)-3-oxo-5,5-dimethyl-1-cyclohexenyl]adipate
(4) bis[2-(2',5'-dimethylphenyl)-3-oxo-1-cyclopentenyl]sebacate
(5) bis[2-(2'-methylphenyl)-3-oxo-5,5-dimethyl-1-cyclohexenyl]terephthalate
(6) bis[2-(2',4'-dichlorophenyl)-3-oxo-1-cyclopentenyl]fumarate
(7) 3-(5-carbomethoxypentanoyloxy)-2-(2',4'-dimethylphenyl)-5,5-dimethyl-2-cyclohexenone
(8) bis[2-(2',4'-dimethylphenyl)-3-oxo-5,5-dimethyl-1-cyclohexenyl]carbonate
(9) bis[2-(2'-chlorophenyl)-3-oxo-1-cyclopentenyl]carbonate
(10) bis[2-(2'-methylphenyl)-3-oxo-4,5,6,7,8,9-hexahydro-1-indenyl]carbonate
(11) [2-(2'-chlorophenyl)-3-oxo-1-cyclopentenyl][2-(2'4'-dimethylphenyl)-3-oxo-5,5-dimethyl-1-cyclohexenyl]carbonate
(12) ethyl[2-(2',4'-dichlorophenyl)-3-oxo-1-cyclohexenyl]carbonate
(13) isopropyl[2-(2',5'-dichlorophenyl)-3-oxo-1-cyclopentenyl]carbonate
(14) [2-ethylhexyl][2-(2',4'-dimethylphenyl)-3-oxo-5,5-dimethyl-1-cyclohexenyl]carbonate
(15) [3,4-dichlorobenzyl][2-(2'-methylphenyl)-3-oxo-5,5-dimethyl-1-cyclohexenyl]carbonate
(16) [benzyl][2-(2',4'-dimethylphenyl)-3-oxo-1-cyclopentenyl]carbonate
(17) [6-chlorohexyl][2-(2'-chlorophenyl)-3-oxo-5,5-dimethyl-1-cyclohexenyl]carbonate
(18) [2-ethylhexyl][2-(2'-methylphenyl)-3-oxo-4,5,6,7,8,9-hexahydro-1-indenyl]carbonate
(19) [2-(2',4'-dimethylphenyl)-3-oxo-5,5-dimethyl-1-cyclohexenyl][isopropyl]thiocarbonate
(20) [2-(2',4'-dichlorophenyl)-3-oxo-1-cyclohexenyl][phenyl]thiocarbonate
(21) [2-(2',4'-dimethylphenyl)-3-oxo-1-cyclopentenyl][n-octyl]thiocarbonate
(22) [2-(2'-methylphenyl)-3-oxo-4,5,6,7,8,9-hexahydro-1-indenyl][t-butyl]thiocarbonate
(23) [2-(2',4'-dimethylphenyl)-3-oxo-4,5,6,7,8,9-hexahydro-1-indenyl][ethyl]thiocarbonate
(24) [2-(2',5'-dimethylphenyl)-3-oxo-1-cyclopentenyl][isobutyl]thiocarbonate
(25) [2-(2',4'-dimethylphenyl)-3-oxo-5,5-dimethyl-1-cyclohexenyl][cyclohexyl]thiocarbonate
(26) [2-(2'-chlorophenyl)-3-oxo-1-cyclohexenyl][benzyl]thiocarbonate
(27) 2-(2',4'-dimethylphenyl)-5,5-dimethyl-3-methoxy-2-cyclohexenone
(28) 2-(2'-methylphenyl)-5,5-dimethyl-3-benzyloxy-2-cyclohexenone
(29) 2-(2',4'-dimethylphenyl)-3-methoxymethoxy-2-cyclopentenone
(30) 2-(2',4'-dimethylphenyl)-3-methoxymethoxy-4,5,6,7,8,9-hexahydro-2-indenone
(31) 2-(2',4'-dichlorophenyl)-3-(2-methoxyethoxy)-5,5-dimethyl-2-cyclohexenone
(32) 2-(2',4'-dimethylphenyl)-3-isobutyloxy-5,5-dimethyl-2-cyclohexenone
(33) 2-(2'-methylphenyl)-3-(methoxymethoxy)-4,5,6,7,8,9-hexahydro-2-indenone
(34) 2-(2',4'-dichlorophenyl)-3-(2-methoxyethoxy)-2-cyclopentenone
(35) 2-(2'-chlorophenyl)-3-(2',4'-dichlorobenzyloxy)-2-cyclopentenone
(36) 2-(2',4'-dimethylphenyl)-3-methoxymethoxy-5-methyl-2-cyclohexenone
(37) bis[2-(2'-methylphenyl)-5,5-tetramethylene-3-oxo-1-cyclohexenyl]carbonate
(38) [2-(2',4'-dimethylphenyl)-5,5-tetramethylene-3-oxo-1-cyclohexenyl][isopropyl]thiocarbonate
(39) [2-(2',4'-dimethylphenyl)-5-methyl-5-n-propyl-3-oxo-1-cyclohexenyl][2-ethylhexyl]carbonate
(40) isopropyl[2(2',4'-dimethylphenyl)-3-oxo-5,5-dimethyl-1-cyclohexenyl]carbonate
(41) [6-chlorohexyl][2(2',4'-dimethylphenyl)-3-oxo-5,5-dimethyl-1-cyclohexenyl]carbonate
(42) benzyl[2(2',4'-dimethylphenyl)-3-oxo-5,5-dimethyl-1-cyclohexenyl]carbonate
(43) [3,4-dichlorobenzyl][2-(2',4'-dimethylphenyl)-3-oxo-5,5-dimethyl-1-cyclohexenyl]carbonate
(44) [2-ethylhexyl][2-(2',4'-dichlorophenyl)-3-oxo-4,4-dimethyl-1-cyclohexenyl]carbonate
(45) [2-ethylhexyl][2-(2'-chlorophenyl)-3-oxo-4,4-dimethyl-1-cyclohexenyl]carbonate
(46) [2-ethylhexyl][2-(2'-chlorophenyl)-3-oxo-1-cyclopentenyl]carbonate
(47) [2-ethylhexyl][2-(2',4'-dichlorophenyl)-3-oxo-1-cyclopentenyl]carbonate
(48) [2-ethylhexyl][2-(2-(2',4'-dimethylphenyl)-3-oxo-1-cyclopentenyl]carbonate
(49) [2-ethylhexyl][2-(2',5'-dimethylphenyl)-3-oxo-4,5,6,7,8,9-hexahydro-1-indenyl]carbonate
(50) [2-(2', 4'-dimethylphenyl)-3-oxo-5,5-dimethyl-1-cyclohexenyl][n-octyl]thiocarbonate
(51) [2-(2',4'-dimethylphenyl)-3-oxo-5,5-dimethyl-1-cyclohexenyl][phenyl]thiocarbonate
(52) 2-(2',4'-dimethylphenyl)-3-(2-methoxyethoxy)-5,5-dimethyl-2-cyclohexenone

(53) 2-(2',4'-dimethylphenyl)-3-benzyloxy-5,5-dimethyl-2-cyclohexenone

(54) 2-(2',4'-dimethylphenyl)-3-methoxymethoxy-5,5-dimethyl-2-cyclohexenone

(55) 2-(2'-methylphenyl)-3-methoxymethoxy-5,5-dimethyl-2-cyclohexenone

(56) 2-(2',4'-dichlorophenyl)-3-methoxymethoxy-5,5-dimethyl-2-cyclohexenone

(57) 2-(2',4'-dimethylphenyl)-3-methoxy-2-cyclohexenone

(58) 2-(2',4'-dimethylphenyl)-3-[2-(2-methoxyethoxyethoxy)]-5,5-dimethyl-2-cyclohexenone.

(59) bis[2-(2',4'-dimethylphenyl)-3-oxo-1-cyclohexenyl]-sebacate.

(60) [2-(2',4'-dimethylphenyl)-3-oxo-5,5-dimethyl-1-cyclohexenyl]-2-(2',5'-dichlorophenyl)-3-oxo-1-cyclopentyl acrbonate.

Selected enol derivatives of 2-phenyl-cycloalkanedione compounds, representative of those useful in accordance with this invention were tested with respect to their miticidal, mite ovicidal and pre-emergent and post-emergent herbicidal activity. It was found that the compounds of the instant invention exhibited improved pesticidal activity, particularly miticidal activity, over structurally similar prior art compounds.

Suspensions of the test compounds were prepared by dissolving one gram of compound in 50 milliliters of acetone in which had been dissolved 0.1 gram (10 percent of the weight of compound) of an alkylphenoxyethoxyethanol sufactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described below were obtained by diluting the stock suspension with water. The test procedures were as follows:

Mite Foliage Spray Test

Adults and nymphal stages of the two-spotted mite (*Tetranychus urticae* (Koch)), reared on Tendergreen bean plants at 80±5° F. and 50±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psi. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5° F. and 50±5 percent relative humidity for four days, after which, a mortality count of motile forms was made on the leaves of the test plants. Any individual which was capable of locomotion upon prodding was considered living.

Mite Ovicide Test

The test organism was the egg of the two-spotted mite (*Tetranychus urticae* (Koch)), as obtained from adults reared on Tendergreen bean plants under controlled conditions of 80±5° F. and 50±5 percent relative humidity. Heavily infested leaves from a stock culture were placed on the primary leaves of two bean plants six to eight inches in height growing in a two-and-a-half inch clay pot. Females were allowed to oviposit for a period of 48 hours and then the leaves of the infested plants were dipped late one afternoon and again the next morning in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly for several hours after the second dipping. The test compounds were formulated by diluting the stock suspension with water to give a suspension containing varying amounts of test compound per million parts of final formulation. The potted plants (one pot per compound) were placed on a revolving turntable and sprayed with 100-110 milliliters of test compound formulation by use of a DeVilbis spray gun set at 40 spig. air pressure. This application which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80±5° F. and 50±5 percent relative humidity for four days, after which a microscopic examination was made of unhatched (dead) and hatched (living) eggs.

In these tests the pesticidal activity of the compounds against mites and mite eggs was rated as follows:

A=Excellent Control
B=Partial Control
C=No Control

| PRELIMINARY HERBICIDE SEED GERMINATION TEST |  |
| --- | --- |
| The following seeds were used in this test: | |
| Perennial rye grass | *Solium perenne* |
| Crabgrass | *Digitaria sanguinalis* |
| Red root pigweed | *Amaranthus retroflexus* |
| Mustard | *Brassica pincea* var. foliosa (Florida broadleaf) |
| Two seed-soil mixtures were prepared as follows: | |
| Mixture I | |
| 196 cc. | Rye grass seed |
| 75 cc. | Mustard seed |
| 18,000 cc. | Sifted, fairly dry soil |
| Mixture II | |
| 99 cc. | Crabgrass seed |
| 33 cc. | Amaranthus |
| 18,000 cc. | Sifted, fairly dry soil |

Each of the above mixtures was rolled separately in 5 gallon containers for approximately one-half hour on ball mill to insure uniform mixing of seeds and soil. For each compound four 3-inch pots were filled with soil to within 1½ inches of top of pots. To two of these pots were added 70 cc. of Mixture I. To the remaining 2 pots were added 70 cc. of Mixture II. The seed-soil mixture was tamped firmly, and the pots were removed to the greenhouse and watered lightly. About 2 hours after planting, 25 milliliters of the test formulation were added to one pot containing Mixture I and one pot containing Mixture II. An equal volume of a water solution containing acetone and an emulsifier in the same concentration as the herbicidal mixture but without the candidate herbicide was also added to each of the soil-seed mixtures. These pots are used as check or control units. The test compounds were formulated by diluting the stock suspension with water to obtain the desired concentration of the compound in parts per million of the final formulation. Each compound was tested at the same concentration. Ten to twelve days after application of the chemical, injury was noted for each species by comparing treated versus untreated pots. Ratings were made according to the following designations:

5 = no seedlings emerged
4 = few seedlings emerged and/or very severe stunting
3 = moderate reduction in stand and/or moderate stunting.
2 = very slight reduction in stand and/or slight stunting
1 = no injury; seedlings appear no different with respect to stand -continued or growth than untreated controls

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solutions to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below. The compound number listed in Table I corresponds to the number of the compound listed on pages 32 to 35.

TABLE I

Biocidal Activity and Physical Properties of Selected Enol Derivatives of 2-Phenyl-1,3-cycloalkanedione Compounds

| Compound Number | M.P.(°C.) or Elemental Analysis | Miticidal | | Post-emergent Herbicidal | | | | | Pre-emergent Herbicidal | | | |
|---|---|---|---|---|---|---|---|---|---|---|---|---|
| | | Adult | Egg | Bean | Corn | Tomato | Cotton | Soybean | Rye | Crab-grass | Amaran-thus | Mustard |
| 7 | Cal'c for: C H $C_{23}H_{30}O_5$ 71.48 7.82 Found: 70.79 7.99 | A | A | 2 | 5 | 2 | 2 | 3 | 5 | 5 | 3 | 5 |
| 3 | 123–125.0 | A | A | 1 | 1 | 1 | 1 | 1 | 5 | 5 | 1 | 2 |
| 59 | Cal'c for: C H $C_{42}H_{54}O_6$ 77.03 8.31 Found: 77.56 8.25 | A | A | 1 | 2 | 1 | 1 | 1 | 5 | 5 | 1 | 1 |
| 8 | 120–122.0 | A | A | 1 | 3 | 1 | 2 | 2 | 5 | 5 | 2 | 4 |
| 40 | Cal'c for: C H $C_{20}H_{26}O_4$ 72.70 7.93 Found: 73.08 7.92 | A | A | 2 | 5 | 1 | 3 | 3 | 5 | 5 | 3 | 1 |
| 41 | Cal'c for: C H $C_{23}H_{31}ClO_4$ 67.88 7.68 Found: 67.72 7.51 | A | A | 1 | 5 | 2 | 4 | 3 | 5 | 5 | 3 | 3 |
| 42 | Cal'c for: C H $C_{24}H_{26}O_4$ 76.16 6.93 Found: 75.91 6.94 | A | A | 1 | 3 | 1 | 1 | 1 | 5 | 5 | 1 | 5 |
| 43 | Cal'c for: C H $C_{24}H_{24}Cl_2O_4$ 64.44 5.41 Found: 64.32 5.24 | A | A | 1 | 1 | 1 | 3 | 1 | 5 | 5 | 2 | 2 |
| 14 | Cal'c for: C H $C_{25}H_{36}O_4$ 74.96 9.06 Found: 75.37 9.20 | A | A | 1 | 5 | 1 | 2 | 2 | 5 | 4 | 1 | 1 |
| 44 | Cal'c for: C H $C_{23}H_{30}Cl_2O_4$ 62.58 6.85 Found: 62.61 6.73 | B | B | 1 | 1 | 1 | 1 | 2 | 1 | 1 | 1 | 1 |
| 45 | Cal'c for: C H $C_{23}H_{31}ClO_4$ 67.88 7.68 Found: 68.25 7.64 | A | A | 2 | 2 | 2 | 2 | 3 | 1 | 1 | 3 | 1 |
| 46 | Cal'c for: C H $C_{20}H_{25}ClO_4$ 65.83 6.91 Found: 66.08 6.81 | A | A | 2 | 3 | 3 | 2 | 2 | 3 | 3 | 2 | 1 |
| 47 | Cal'c for: C H $C_{20}H_{24}Cl_2O_4$ 60.15 6.06 Found: 61.11 6.00 | A | A | 2 | 4 | 1 | 2 | 2 | 1 | — | 1 | 1 |
| 48 | Cal'c for: C H $C_{22}H_{30}O_4$ 73.71 8.44 Found: 73.84 8.42 | A | A | 1 | 1 | 1 | 1 | 1 | 3 | 3 | 1 | 1 |
| 49 | Cal'c for: C H $C_{26}H_{36}O_4$ 75.69 8.80 Found: 75.87 8.78 | A | A | 2 | 2 | 1 | 1 | 1 | 1 | 1 | 1 | 1 |

TABLE I-continued

Biocidal Activity and Physical Properties of Selected
Enol Derivatives of 2-Phenyl-1,3-cycloalkanedione Compounds

| Compound Number | M.P.(°C.) or Elemental Analysis | | | Miticidal | | Post-emergent Herbicidal | | | | | Pre-emergent Herbicidal | | | |
|---|---|---|---|---|---|---|---|---|---|---|---|---|---|---|
| | | | | Adult | Egg | Bean | Corn | Tomato | Cotton | Soybean | Rye | Crab-grass | Amaran-thus | Mustard |
| 18 | Cal'c for: | C | H | A | A | 1 | 2 | 1 | 2 | 2 | 4 | 3 | 2 | 3 |
| | $C_{25}H_{34}O_4$ | 75.34 | 8.60 | | | | | | | | | | | |
| | Found: | 75.44 | 8.56 | | | | | | | | | | | |
| 19 | Cal'c for: | C | H | A | A | 1 | 5 | 1 | 2 | 3 | 5 | 5 | 3 | 3 |
| | $C_{20}H_{26}O_3S$ | 69.33 | 7.56 | | | | | | | | | | | |
| | Found: | 69.36 | 7.57 | | | | | | | | | | | |
| 50 | Cal'c for: | C | H | A | A | — | 2 | — | 1 | 1 | 5 | — | — | 1 |
| | $C_{25}H_{36}O_3S$ | 72.07 | 8.71 | | | | | | | | | | | |
| | Found: | 72.12 | 8.68 | | | | | | | | | | | |
| 51 | Cal'c for: | C | H | A | A | — | 4 | — | 2 | 1 | 5 | — | — | 2 |
| | $C_{23}H_{24}O_3S$ | 72.60 | 6.36 | | | | | | | | | | | |
| | Found: | 72.77 | 6.15 | | | | | | | | | | | |
| 52 | Cal'c for: | C | H | A | A | 2 | 3 | 2 | 2 | 2 | 5 | 5 | 1 | 1 |
| | $C_{19}H_{26}O_3$ | 75.46 | 8.67 | | | | | | | | | | | |
| | Found: | 75.30 | 8.55 | | | | | | | | | | | |
| 58 | Cal'c for: | C | H | A | A | 2 | 3 | 2 | 1 | 2 | 5 | 5 | 1 | 3 |
| | $C_{21}H_{30}O_4$ | 72.80 | 8.73 | | | | | | | | | | | |
| | Found: | 72.51 | 8.47 | | | | | | | | | | | |
| 32 | Cal'c for: | C | H | C | B | 1 | 1 | 1 | 1 | 1 | 1 | 1 | 1 | 1 |
| | $C_{20}H_{28}O_2$ | 79.96 | 9.39 | | | | | | | | | | | |
| | Found: | 80.19 | 9.37 | | | | | | | | | | | |
| 53 | Cal'c for: | C | H | A | A | 1 | 1 | 2 | 1 | 2 | 5 | 1 | 1 | 3 |
| | $C_{23}H_{26}O_2$ | 82.60 | 7.83 | | | | | | | | | | | |
| | Found: | 82.46 | 7.79 | | | | | | | | | | | |
| 54 | Cal'c for: | C | H | A | A | 2 | 5 | 1 | 2 | 2 | 5 | 5 | 4 | 3 |
| | $C_{18}H_{24}O_3$ | 74.97 | 8.39 | | | | | | | | | | | |
| | Found: | 74.64 | 8.22 | | | | | | | | | | | |
| 55 | Cal'c for: | C | H | A | A | 2 | 5 | 1 | 2 | 3 | 5 | 5 | 3 | 3 |
| | $C_{17}H_{22}O_3$ | 74.42 | 8.08 | | | | | | | | | | | |
| | Found: | 74.71 | 8.17 | | | | | | | | | | | |
| 56 | | | | A | A | 2 | 5 | 1 | 2 | 3 | 5 | 3 | 3 | 3 |
| 30 | Cal'c for: | C | H | A | A | 3 | 4 | 2 | 4 | 3 | 5 | 5 | 4 | 4 |
| | $C_{19}H_{24}O_3$ | 75.97 | 8.05 | | | | | | | | | | | |
| | Found: | 75.67 | 8.00 | | | | | | | | | | | |
| 57 | Cal'c for: | C | H | C | C | 1 | 1 | 1 | 1 | 1 | 4 | 1 | 1 | 1 |
| | $C_{17}H_{22}O_2$ | 79.03 | 8.58 | | | | | | | | | | | |
| | Found: | 79.15 | 8.57 | | | | | | | | | | | |

What is claimed is:

1. A compound of the formula:

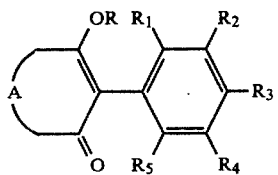

wherein: R is

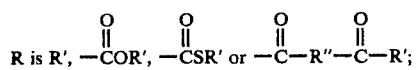

wherein:

R' may not include more than thirty aliphatic carbons and is selected from: an unsubstituted or substituted alkyl, alkenyl, alkynyl, bicycloalkyl, bicycloalkenyl, cycloalkyl, cycloalkenyl, phenyl, phenylalkyl, naphthyl, or naphthylalkyl group wherein the permissible substituents are one or more alkyl, cyano, nitro, alkoxy, aryloxy, halogen, haloalkyl, alkylthio, arylthio, alkylsulfinyl, arylsulfinyl, alkylsulfonyl, arylsulfonyl alkoxyalkyl, aryloxyalkyl, alkylthioalkyl, arylthioalkyl, arylsulfinylalkyl, alkylsulfinylalkyl, alkylsulfonylalkyl, arylsulfonylalkyl, or dialkylamino groups in any combination;

R" is a divalent moiety which may not include more than thirty aliphatic carbon atoms and is selected from an unsubstituted or substituted alkylene, alkenylene, alkynylene, bicycloalkylene, bicycloalkenylene, cycloalkylene, cycloalkenylene, phenylene, phenylalkylene, naphthylene, or naphthylalkylene group wherein the permissible substituents are one or more alkyl, cyano, nitro, alkoxy, aryloxy, halogen, haloalkyl, alkylthio, arylthio, alkylsulfinyl, arylsulfinyl, alkylsulfonyl, arylsulfonyl alkoxyalkyl, aryloxyalkyl, alkylthioalkyl, arylthioalkyl, alkylsulfinylalkyl, arylsulfinylalkyl, alkylsulfonylalkyl, arylsulfonylalkyl or dialkylamino groups, in any combination;

$R_1$ may not individually include more than ten aliphatic carbon atoms and is an alkyl, haloalkyl, halogen or polyhaloalkyl group;

$R_2$, $R_3$, $R_4$ and $R_5$ may not individually include more than ten aliphatic carbon atoms and are individually hydrogen, nitro, polyhaloalkyl, halogen, cyano, alkyl, alkoxy, alkylthio, alkylsulfinyl, alkylsulfonyl, alkanoyl amido, amino or haloalkyl groups;

A is an alkylene or alkenylene chain containing two or three carbon atoms which may be substituted by one or more substituents which may be the same or different selected from:

(a) substituents which may not include more than ten aliphatic carbon atoms selected from: an alkyl, alkenyl, cycloalkyl or cycloalkenyl groups, which groups may be further substituted with one or more cyano, halogen, nitro, alkoxy, aryloxy, alkylthio, arylthio, alkylsulfinyl, arylsulfinyl, alkylsulfonyl, arylsulfonyl, acylamido, or dialkylamino substituents in any combination; and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents in any combination;

(b) a divalent alkylene or alkenylene group having from 2 to 20 carbon atoms completing a 3,4,5,6 or 7 membered carbon ring with the proviso that when A is a hydrocarbon chain containing two carbon atoms, said hydrocarbon chain may not form together with said divalent alkylene group a six membered fused polycyclic ring structure wherein said six membered ring has more than two double bonds.

2. A compound according to claim 1 wherein:
R' may not include more than 18 aliphatic carbon atoms and is selected from an alkyl, alkenyl, alkynyl, phenyl, phenylalkyl, naphthyl or naphthylalkyl group, all of which may be unsubstituted or substituted with one or more chloro, alkoxy, alkylthio or alkyl groups in any combination; and
R" is a divalent moiety which may not include more than 18 aliphatic carbon atoms and is selected from an alkylene, alkenylene, alkynylene, phenylene, phenylalkylene, naphthylene or naphthylalkylene group all of which may be unsubstituted or substituted with one or more chloro, alkoxy, alkylthio or alkyl groups in any combination.

3. A compound according to claim 2 wherein:
$R_2$, $R_3$, $R_4$ and $R_5$ are individually hydrogen, alkyl, cyano, alkoxy, halogen or trihalomethyl groups.

4. A compound according to claim 3 wherein A is a saturated hydrocarbon group containing three carbon atoms which group may be substituted by one or more $C_1-C_6$ alkyl groups.

5. A compound according to claim 4 wherein:
$R_1$ is an alkyl or halogen;
$R_2$, $R_4$ and $R_5$ are hydrogen; and
$R_3$ is an alkyl or halogen.

6. A compound according to claim 5 wherein:
R' is a $C_1-C_{18}$ alkyl group; a phenyl group; or a $C_7-C_{12}$ phenylalkyl group
R" is a $C_1-C_{18}$ alkylene group; a phenyl group; or a $C_7-C_{12}$ phenylalkyl group.

7. A compound according to claim 6 wherein $R_1$ and $R_3$ are individually methyl or chlorine.

8. A compound according to claim 7 wherein R is:

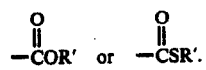

9. A compound according to claim 8 wherein

10. A compound of the formula:

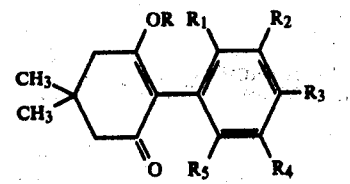

wherein: R is

wherein:
R' may not include more than 18 aliphatic carbon atoms and is selected from an alkyl, alkenyl, alkynyl, phenyl, phenylalkyl, naphthyl or naphthylalkyl group all of which may be unsubstituted or substituted with one or more chloro, alkoxy, alkylthio or alkyl groups in any combination;
R" is a divalent moiety which may not include more than 18 aliphatic carbon atoms and is selected from an alkylene, alkenylene, alkynylene, phenylene, phenylalkylene, naphthylene or naphthylalkylene group all of which may be unsubstituted or substituted with one more more chloro, alkoxy, alkylthio, or alkyl groups, in any combination.

11. A compound according to claim 10 wherein:
$R_2$, $R_3$, $R_4$ and $R_5$ are individually hydrogen, alkyl, cyano, alkoxy, halogen or trihalomethyl groups.

12. A compound according to claim 11 wherein:
$R_1$ is an alkyl or halogen;
$R_2$, $R_4$ and $R_5$ are hydrogen; and
$R_3$ is an alkyl or halogen.

13. A compound-ccording to claim 12 wherein:
R' is a $C_1-C_{18}$ alkyl group unsubstituted or substituted with one or two alkoxy groups or one chloro group; a phenyl group; or a $C_7-C_{12}$ phenylalkyl group unsubstituted or substituted with one or two chloro groups;
and
R" is a $C_1-C_{18}$ alkylene group unsubstituted or substituted with one or two alkoxy groups or one chloro group; a phenyl group; or a $C_7-C_{12}$ phenylalkyl group unsubstituted or substituted with one or two chloro group.

14. A compound according to claim 13 wherein $R_3$ is methyl or chlorine.

15. A compound according to claim 14 wherein $R_1$ is methyl or chlorine.

16. A compound according to claim 15 wherein

17. A compound according to claim 16 wherein

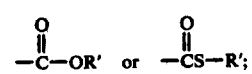

and R' is selected from the group consisting of

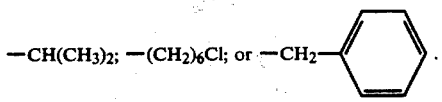

18. A compound according to claim 17 wherein

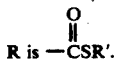

19. [2-(2',4'-dimethylphenyl)-3-oxo-5,5-dimethyl-1-cyclohexenyl][isopropyl]thiocarbonate.
20. [2-(2'-methylphenyl)-3-oxo-5,5-dimethyl-1-cyclohexenyl][phenyl]thiocarbonate.
21. A compound of the formula:

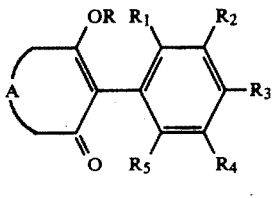

wherein:

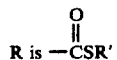

wherein:
R' may not include more than thirty aliphatic carbons and is selected from: an unsubstituted or substituted alkyl, alkenyl, alkynyl, bicycloalkyl, bicycloalkenyl, cycloalkyl, cycloalkenyl, phenyl, phenylalkyl, naphthyl, or naphthylalkyl group wherein the permissible substituents are one or more alkyl, cyano, nitro, alkoxy, aryloxy, halogen, haloalkyl, alkylthio, arylthio, alkylsulfinyl, arylsulfinyl, alkylsulfonyl, arylsulfonyl, alkoxyalkyl, aryloxyalkyl, alkylthioalkyl, arylthioalkyl, arylsulfinylalkyl, alkylsulfinylalkyl, alkylsulfonylalkyl, arylsulfonylalkyl or dialkylamino groups in any combination;

$R_1$ may not individually include more than ten aliphatic carbon atoms and is an alkyl, haloalkyl, halogen or polyhaloalkyl group;

$R_2$, $R_3$, $R_4$ and $R_5$ may not individually include more than ten aliphatic carbon atoms and are individually hydrogen, nitro, polyhaloalkyl, halogen, cyano, alkyl, alkoxy, alkylthio, alkylsulfinyl, alkylsulfonyl, alkanoyl amido, amino or haloalkyl groups;

A is an alkylene or alkenylene chain containing two or three carbon atoms which may be substituted by one or more substituents which may be the same or different selected from:

(a) substituents which may not include more than ten aliphatic carbon atoms selected from: an alkyl, alkenyl, cycloalkyl or cycloalkenyl groups, which groups may be further substituted with one or more cyano, halogen, nitro, alkoxy, aryloxy, alkylthio, arylthio, alkylsulfinyl, arylsulfinyl, alkylsulfonyl, arylsulfonyl, acylamido, or dialkylamino substituents in any combination; and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents in any combination;

(b) a divalent alkylene or alkenylene group having from 2 to 20 carbon atoms completing a 3,4,5,6 or 7 membered carbon ring with the proviso that when A is a hydrocarbon chain containing two carbon atoms, said hydrocarbon chain may not form together with said divalent alkylene group a six membered fused polycyclic ring structure wherein said six membered ring has more than two double bonds.

* * * * *